US00PP14432P29

(12) United States Plant Patent
Colfer

(10) Patent No.: US PP14,432 P2
(45) Date of Patent: Dec. 30, 2003

(54) ARTICHOKE PLANT NAMED 'PS-IG0060'

(50) Latin Name: *Cynara scolymus L.*
Varietal Denomination: PS-IG0060

(75) Inventor: William J. Colfer, Aptos, CA (US)

(73) Assignee: Plant Sciences, Inc., Watsonville, CA (US)

( * ) Notice: Subject to any disclaimer, the term of this patent is extended or adjusted under 35 U.S.C. 154(b) by 0 days.

(21) Appl. No.: 10/251,981

(22) Filed: Sep. 23, 2002

(51) Int. Cl.[7] ..... A01H 5/00
(52) U.S. Cl. ..... Plt./258

(58) Field of Search ..... Plt./258

(56) References Cited

U.S. PATENT DOCUMENTS

PP12,210 P2 * 11/2001 Colfer ..... Plt./258

* cited by examiner

*Primary Examiner*—Bruce R. Campell
*Assistant Examiner*—W C Haas
(74) *Attorney, Agent, or Firm*—Foley & Lardner

(57) ABSTRACT

A new and distinct cultivar of artichoke plant named 'PS-IG0060', characterized by its numerous bud numbers, fleshiness of bracts, fleshiness of hearts, uniformity of head shapes.

3 Drawing Sheets

Latin name of the genus and species of the plant claimed: *Cynara scolymus* L.
Variety denomination: PS-IG0060.

BACKGROUND OF THE INVENTION

The present invention comprises a new and distinct cultivar of artichoke plant, botanically known as *Cynara scolymus* L. and herein referred to by the cultivar name 'PS-IG0060'.

*Cynara scolymus* L., commonly known as Globe artichoke, is a thistle-like perennial herb and is a member of the family Asteraceae. Globe artichokes comprise leaves which are pinnately lobed but primarily spineless, globose capitula composed of overlapping layers of large volucral bracts, and receptacles which are enlarged and fleshy. Globe artichoke plants may be propagated by division and are essentially grown for the production of the immature flower heads, which are considered as vegetable delicacies. Fresh artichokes may be steamed or boiled, after which the fleshy receptacle, inner and outer bracts, and parts of the floral stem may be eaten.

BRIEF SUMMARY OF THE INVENTION

The new cultivar is a product of a planned breeding program carried out by the inventor, William J. Colfer at Chowchilla, Calif. in 1997. The female parent is CTC6 (seed parent) and the male parent is GGMSSC5 (pollen parent). The new cultivar was discovered from the progeny of the stated cross by William J. Colfer and was asexually propagated for the first time in 1997 in Watsonville, Calif.

Asexual propagation by division has demonstrated the stability of the combination of characteristics of the new cultivar from generation to generation.

The new cultivar has not been observed under all possible environmental conditions. The phenotype may vary with variations in environment such as temperature, light intensity and daylength, without any change in the genotype of the cultivar.

BRIEF DESCRIPTION OF THE DRAWINGS

The accompanying photographic drawings show fruit and leaves from a typical specimen plant of 'PS-IG0060', with color being depicted as possible with illustrations of this type.

The first drawing is a side view of the fruit and foliage of 'PS-IG0060'.

The second drawing is a close-up view of the fruit showing its physical dimensions.

The third drawing is a close-up view showing a vertical cross-section of the fruit.

DETAILED BOTANICAL DESCRIPTION

The following observations, measurements and values describe plants of 'PS-IG0060' grown in Chowchilla, Calif. under conditions which closely approximate those generally used in horticultural practice. The age of the plants described is approximately 348 days (228 days from transplanting and an additional 120 days developed in transplant trays).

All color references below are measured against The Munsell Book of Color, Munsell Color Macbeth Division of Kollomogen Corporation. Colors are approximate as color depends on horticultural practices such as light level and fertilization rate, among others.

Chowchilla is located in California's central San Juaquin valley. Conditions can vary greatly during the summer months. Air temperature can range between the low 20's (degrees Fahrenheit) in the winter to well above the 100 (degrees Fahrenheit) during the summer months. Relative humidity is generally low with values ranging from the mid 40's to the high 60's. Prevailing winds are westerly and rainfall rarely exceeds 15" (inches) of rainfall.

In the following description, holding quality was measured by the physical appearance of the harvested heads. This includes the heads appearance following 3, 7 and 10 day storage periods in a cold storage room held at 34 (degrees Fahrenheit). Head exterior (oxidation) was observed at each of the three observation points. Browning and blackening of plant tissue was evaluated as light, moderate and extreme. Juiciness was measured by observing exudate and rated as absent, moderate or excessive. Overall storage response was measured by observations concentrated on visible color variability and / or presence of lesions or other cosemetic anomalies. Leaf ratio (L/W) was determined by dividing representative leaf sample length measurements by representative leaf sample width measurements. Finally, head response to (weather) was determined by observing the heads at maturity. These field observations focus on presence or absence of bronzing, necrotic and chlorotic lesions or any abiotic response to environmental conditions. These data are reported as the possible causal event(s) and then describe the detailed head and plant responses.

It should be noted that these data were collected from first year tissue culture outplants. The method of tissue culture used in propagation was standard micropropagation methodology.

These data are subject to change in the plant's future growth and development. The new and distinct cultivar of artichoke plant named 'PS-IG0060' is characterized by:

1. numerous bud numbers;
2. fleshiness of bracts;
3. fleshiness of hearts; and
4. uniformity of head shapes.

The date of first harvest is approximately May 28 and the date of final harvest is approximately June 17, depending on environmental conditions. Plant growth from November to February is moderate, dependent upon environmental and agronomic conditions. Plant growth and development from March to June is rapid, dependent upon environmental and agronomic conditions, with sexual stages initiating in late April.

TABLE 1

| | |
|---|---|
| Parentage: | |
| Male parent: | GGMSSC5 (pollen parent) |
| Female parent: | CTC6 (seed parent) |
| Classification: | Botanical: *Cynara scolymus* L.<br>Commercial: artichoke c.v. PS-IG0060 |
| Propagation: | Asexual production either by tissue culture (standard micropropagation methodology) or division |
| Plant: | |
| Height: | $\bar{x}$ = 104.39 cm<br>range: 100.33–111.76 cm |
| Growth Habit: | Upright/intermediate |
| Dimensions: | $\bar{x}$ = 104.39 cm (h) × 215.39 cm (w)<br>range: 100.33–111.76 cm (h) × 203.20–238.76 cm (w) |
| Side Shoots: | $\bar{x}$ = 5.20<br>range: 3.0–7.0 |
| Length of Side Shoots | Between 17–36.5 cm |
| Diameter of Side Shoots | Between 3.4–5.2 cm |
| Foliage Density: | Dense, multiple shoots give plant a high density appearance |
| Side Shoot Development: | Vigorous side shoot development |
| Number of Leaves on Side Shoot: | Between 6–10 |
| Main Stem Length: | Between 40–56 cm |
| Main Stem Diameter: | Between 4.5–6.7 cm |
| Number of Leaves on Main Stem: | Between 16–30 |
| Capitulum: | |
| Size: | Primary: 36.20–38.10 cm<br>Secondary: 28.58–30.40 cm |

TABLE 1-continued

| | |
|---|---|
| Shape: | Oval. Oval shape can have increased midsection dimensions |
| Number: | $\bar{x}$ = 12.8/plant<br>range: 7.0–16.0 heads/plant |
| Texture: | Intermediate, smooth |
| Fragrance: | Mild, lightly aromatic |
| Bract Size: | $\bar{x}$ = 7.76 cm (l) × 6.20 cm (w)<br>range: 6.5–8.0 cm (l) × 5.6–6.5 cm (w) |
| Bract Shape: | Bracts are predominantly oval shaped with constricted (narrow) basal regions |
| Bract Texture; | Smooth, slight texture |
| Bract Number: | $\bar{x}$ = 80.20 bracts<br>range: 78–82 bracts |
| Bract Color: | Inner: 5 Y 9/6<br>Outer: 5 GY 6/6–5 GY 6/4 |
| Bract Basal Thickness: | $\bar{x}$ = 6.50 mm<br>range: 5.0–8.0 mm |
| Heart Description: | Concave, full. Heart is nearly flat, very little concave quality |
| Heart Color: | 5 Y 9/1–5 Y 9/2 |
| Papus Length: | $\bar{x}$ = 17.67 mm<br>range: 15.0–20.0 mm |
| Papus Color: | Variable white coloration |
| Overall Cold Storage Response: | Good cold storage response; slight oxidation observed (light browning) |
| Head Firmness: | Heads are very firm |
| Bract Firmness: | Moderate. Bracts are quite malleable especially outer bract tissue |
| Gloss: | Semi-gloss; younger heads have a slightly greater glossiness |
| Cold Storage (hold quality): | Good; only a slight "browning" was observed on some bract edges |
| Head Exterior (oxidation): | Moderate; only those areas damaged during harvest showed some oxidation |
| Juiciness: | Moderate presence; peduncle and bract exudate is only moderate |
| Head Response (weather): | None; no adverse plant responses were observed |
| Bud Burst: | Between May 8 and June 17 |
| Bud Weight: | Between 447.65 and 468.90 grams; average 452.73 grams per head |
| Bloom Time: | Between June 2 and June 23 |
| Bloom Duration: | Approximately 35 days |
| Bloom Diameter: | Between 7.5 to 9.2 cm |
| Bloom Depth: | Between 11–11.7 cm |
| Bloom Shape: | Head (slightly rounded oval) |
| Floret Number Per Bloom: | Approximately 1362 to 1482 |
| Floret Size: | Between 8.5–9.8 cm in length<br>Between 3 and 3.1 mm in width |
| Floret Color: | Range between 2.5P 5/8–2.5P 5/10–2.5P 4/10 |
| Seeds: | |
| Shape: | Ovate |
| Size: | 0.7–0.8 mm in length; 0.35–0.4 in width |
| Number: | Highly variable between 61–509; average 244 seeds per head |
| Color: | Variable; light brown hues with moderate speckling; darker tan hues with speckled pattern |
| Foliage: | |
| Shape: | Irregularly dentate, pinnatisect, reduced tomentose and mucronulate |
| Length: | $\bar{x}$ = 122.16 cm<br>range: 104.0–138.0 cm |
| Width: | $\bar{x}$ = 77.80 cm<br>range: 70.0–84.0 cm |
| Leaf Serrations: | $\bar{x}$ = 32.86 mm<br>range: 24.0–38.0 mm |
| Leaf Basal Angle: | $\bar{x}$ = 32.86 degrees<br>range: 25.0–40.0 degrees |
| Leaf Ratio (L/W): | $\bar{x}$ = 1.55<br>range: 1.23–1.78 |

TABLE 1-continued

| | |
|---|---|
| Leaf Area: | $\bar{x}$ = 9,512.0 $cm^2$<br>range: 7696–11316 $cm^2$ |
| Color: | 5 GY 4/4–5 GY 3/6 |
| Texture: | Slightly textured. Immature developing leaves are smooth. Older leaves blistered-rough surface. |
| Veination: | Prominent, white. Both midvein and surrounding veination are white colored. |
| Pubescence: | Moderate density. Pubescence on most leaves is prominent. |
| Leaf Basal Thickness: | $\bar{x}$ = 20.01 mm<br>range: 17.0–25.0 mm |
| Leaf Distance Between Serrations: | $\bar{x}$ = 45.22 mm<br>range: 30.0–64.0 mm |
| Petiole Length: | $\bar{x}$ = 19.95 cm<br>range: 18.5–21.8 cm |
| Petiole Width: | $\bar{x}$ = 38.30 mm<br>range: 30.0–46.0 mm |
| DISEASE RESISTANCE: | No observations made |

GENERAL OBSERVATIONS

This new artichoke cultivar is a unique type that exhibits the following characteristics. The plants moderate height, ranging from 100–111 cm. Its comparative head qualities to California's artichoke variety Green Globe include: green (non-glossy) exterior coloration, comparable head numbers. Head numbers ranging from 7–16 heads per plant. Head shape does not vary displaying an oval shape. These non-glossy heads are produced in the sizes ranging from (18) primary, size (30) secondaries and size (48) tertiaries. Floral stalk development and head numbers can vary. Anthocyanin coloration is present in innermost interior bracts and found on only some outer, exterior bract edges. Its presence is characterized as light. The head spinosity is slightly more prominent on these notched bracts. The average spine length ranges between 0.5–1.0 mm. The plants upright growth habit is intermediate, but is very vigorous. The canopies coloration is a deeper green/green/yellow color with some colors ranging towards darker green/ green/ grey hues. These colors on Munsell Leaf Color Chart range from 5 GY 4/4–5 GY 3/6. Leaf spinosity is light to moderate, categorized as few. Floral stalk development during anthesis produces a purple flower. Flower color varies with flower maturity. The phenotypic characteristics of this cultivar may vary slightly, depending upon variation in the environmental factors. Including weather (temperature, humidity and light intensity), day length, soil type, farming practices, location and time of year.

I claim:

1. A new and distinct cultivar of artichoke plant named 'PS-IG0060', as described and illustrated.

* * * * *

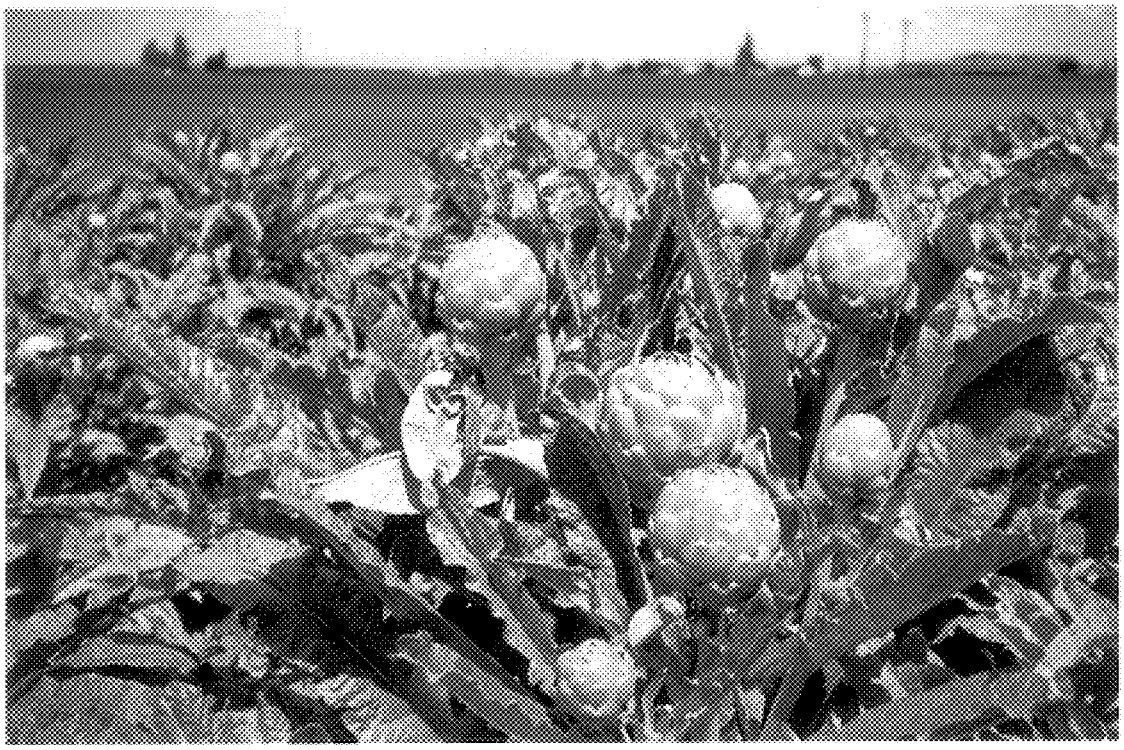

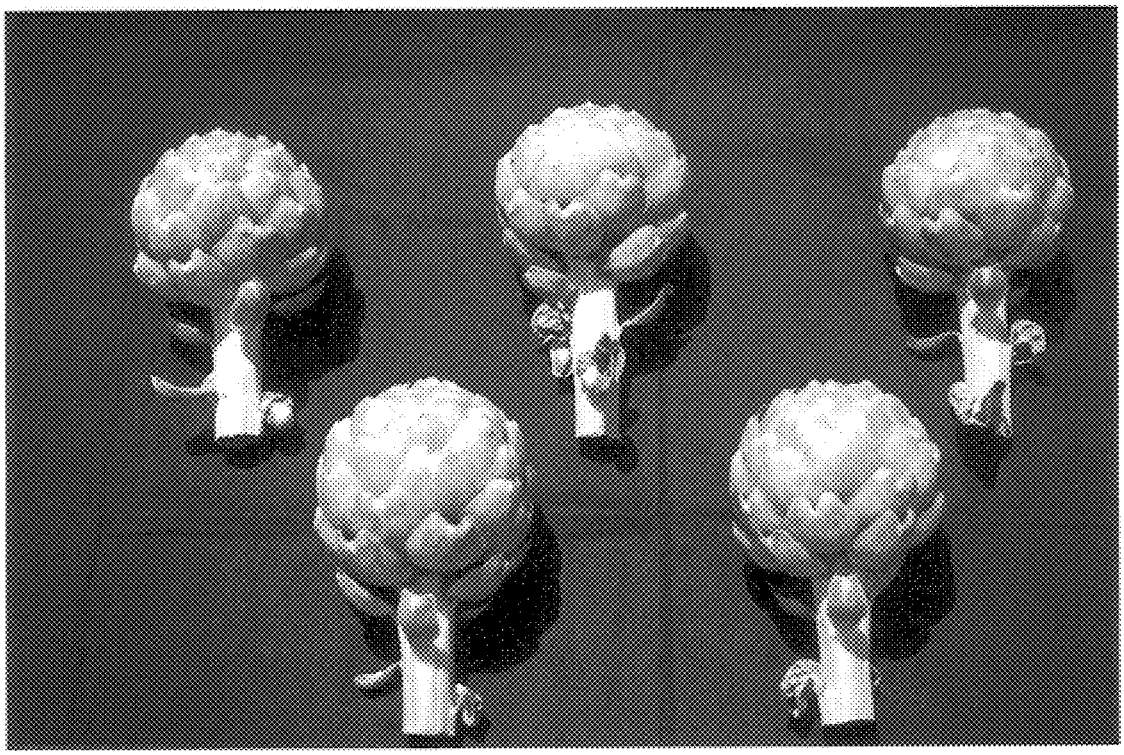

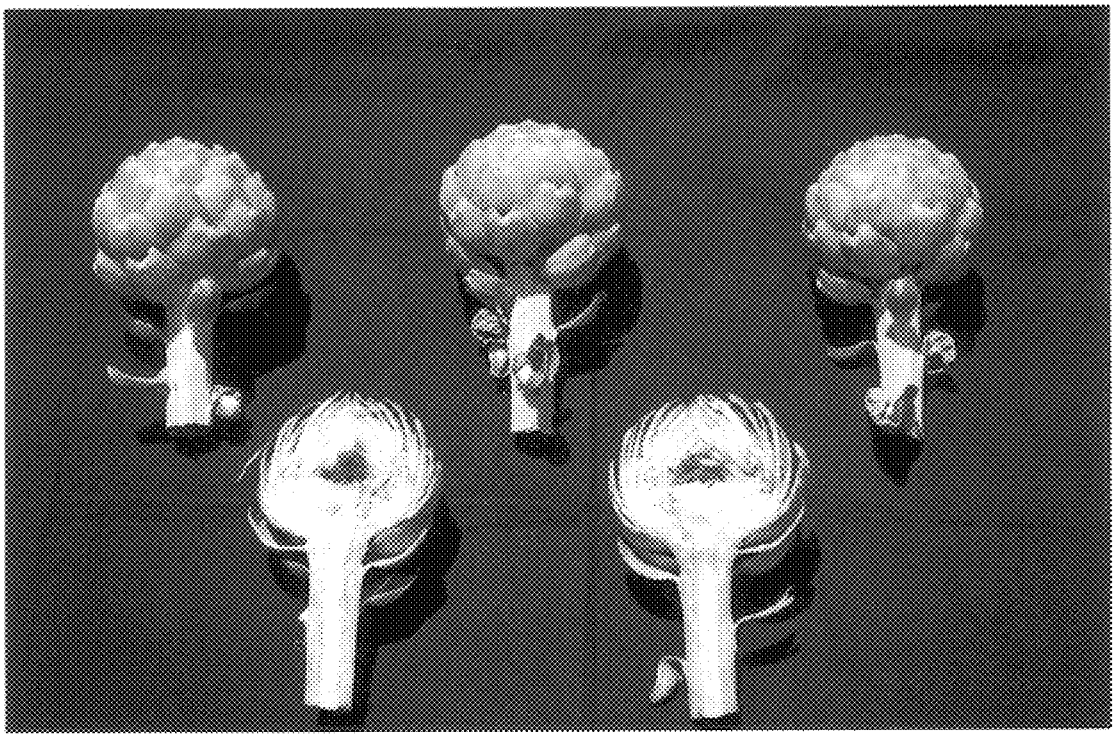

UNITED STATES PATENT AND TRADEMARK OFFICE

CERTIFICATE OF CORRECTION

PATENT NO. : PP 14,432 P2
DATED : January 22, 1998
INVENTOR(S) : Colfer

It is certified that error appears in the above-identified patent and that said Letters Patent is hereby corrected as shown below:

Title page,
Item [73], Assignee, please add -- Seed Research Services, LLC
Salinas, CA --

Signed and Sealed this

Twenty-sixth Day of July, 2005

JON W. DUDAS
*Director of the United States Patent and Trademark Office*